United States Patent
Gilmutdinov et al.

[11] Patent Number: 5,981,912
[45] Date of Patent: Nov. 9, 1999

[54] ELECTROTHERMAL ATOMIZATION MEANS FOR ANALYTICAL SPECTROMETRY

[75] Inventors: Albert Gilmutdinov, Kazan, Russian Federation; Michael Sperling, Sipplingen; Bernhard Welz, Uhldingen, both of Germany

[73] Assignee: Bodenseewerk Perkin-Elmer GmbH, Uberlingen, Germany

[21] Appl. No.: 09/151,571

[22] Filed: Sep. 11, 1998

Related U.S. Application Data

[62] Division of application No. 08/792,322, Jan. 31, 1997, Pat. No. 5,866,431.

[30] Foreign Application Priority Data

Feb. 1, 1996 [DE] Germany .................. 196 03 643

[51] Int. Cl.⁶ .................. F27B 17/02; F27D 11/02; G01N 1/22; G01N 21/74; H05B 3/10
[52] U.S. Cl. .................. 219/398; 392/395; 392/409; 73/863.11; 73/863.12; 73/864.81; 356/312; 422/78; 436/157; 436/181
[58] Field of Search .................. 219/385, 388, 219/390, 391, 392, 395, 398, 407, 409, 427, 656; 73/863.11, 863.12, 864.81; 356/312; 422/78, 107; 436/157, 177, 181; 392/478

[56] References Cited

U.S. PATENT DOCUMENTS

| | | | |
|---|---|---|---|
| 3,862,805 | 1/1975 | Tamm et al. | 356/244 |
| 4,039,794 | 8/1977 | Kasper | 219/656 |
| 4,111,563 | 9/1978 | Tamm | 356/244 |
| 4,162,849 | 7/1979 | Huber | 356/312 |
| 4,204,769 | 5/1980 | Lersmacher et al. | 356/312 |
| 4,247,735 | 1/1981 | Rigatti-Luchini | 219/427 |
| 4,406,541 | 9/1983 | Tomoff et al. | 356/312 |
| 4,407,582 | 10/1983 | Woodriff | 356/312 |
| 4,578,564 | 3/1986 | Ando | 392/478 |
| 4,579,451 | 4/1986 | Lersmacher | 356/312 |
| 4,826,318 | 5/1989 | Guenther et al. | 356/312 |
| 4,834,536 | 5/1989 | Tamm et al. | 356/312 |
| 4,968,141 | 11/1990 | Tamm et al. | 356/312 |
| 4,971,438 | 11/1990 | Hutsch et al. | 356/312 |
| 5,083,864 | 1/1992 | Huetsch et al. | 356/312 |
| 5,247,841 | 9/1993 | Ulrich et al. | 73/864.81 |

FOREIGN PATENT DOCUMENTS 3528439  2/1987  Germany .

*Primary Examiner*—Joseph Pelham
*Attorney, Agent, or Firm*—David Aker; Joseph V. Gamberdell, Jr.

[57] ABSTRACT

An electrically heatable hollow-body furnace with a secondary surface on which an analyte of a sample can be condensed prior to being atomized. The furnace is constructed in two sections which are capable of being electrically heated independently of one another. The secondary surface is defined by a surface of one of the sections. A process for atomizing an analyte of a sample to be examined, utilizing the device according to the following steps: introducing the sample into a hollow-body furnace having a secondary surface, condensing the analyte on the secondary surface and atomizing the analyte.

10 Claims, 2 Drawing Sheets

ELECTROTHERMAL ATOMIZATION MEANS FOR ANALYTICAL SPECTROMETRY

This application is a Divisional application of U.S. patent application Ser. No. 08/792,322, filed on Jan. 31, 1997, now U.S. Pat. No. 5,866,431.

FIELD OF THE INVENTION

The present invention refers to an atomization means for converting an analyte of a sample to be examined into the atomized state, said atomization means comprising an electrically heatable hollow-body furnace including a secondary surface on which an analyte of a sample to be examined can be condensed prior to being converted into the atomized state for examination.

Furthermore, the present invention refers to a process for atomizing an analyte of a sample to be examined, said process comprising the following steps: introducing the sample into a hollow-body furnace having a secondary surface, condensing the analyte on said secondary surface and atomizing the analyte.

BACKGROUND ART

Such a device and such a process are known from the publication "Electrothermal atomic absorption spectrometry by reatomization from a second trapping surface" by P. Hocquellet in Spectrochimica Acta, 47B, pages 719–729, 1992, and also from T. M. Rettberg and J. A. Holcombe, Spectrochimica Acta, 41B, pages 377–389, 1986.

The known atomization means is shown in FIG. 4. It comprises a heatable tubular furnace 1 which consists of graphite and which has provided therein an additional element 60 of graphite having an arched surface 50. An analyte of a sample to be examined can be condensed on this arched surface, the socalled secondary surface. The known furnace is heated by conducting a current in the longitudinal direction through the tubular part of the furnace by means of existing contact members (not shown). When the furnace is being heated, the analyte is atomized and condensed on the secondary surface.

When said secondary surface has reached the temperature of the furnace atmosphere, the analyte is reatomized.

By means of an arrangement and a process of the above-mentioned type, the matrix effects occurring during atomization can be reduced significantly in view of the redistribution of the analyte. Furthermore, due to the condensation of the analyte on the secondary surface, the reatomization of the analyte is essentially based on desorption from said surface. It follows that this atomization is essentially independent of the original composition of the sample.

SUMMARY OF THE INVENTION

It is the object of the present invention to improve the known device and the known process in such a way that improved examination results are obtained.

For a device of the type referred to at the beginning, this object is achieved by the feature that the the furnace comprises a first section and a second section, which are adapted to be electrically heated independently of one another, the secondary surface being defined by a surface of said first section.

This permits a separate, precise temperature control of the two sections of the furnace, said temperature control being possible with regard to the heating rates as well as with regard to the respective final temperatures. The heating program can be adapted to the analytical requirements in the best possible manner in this way.

In particular, this structural design permits a much better control of the temperatures of the gaseous phase and of the surfaces of the atomizer. Due to the fact that the secondary surface is controlled separately, the time delay in the heating of the atomization surface can be controlled independently of the aimed-at final temperature.

Furthermore, in contrast to the passive function of the secondary surface in the prior art, the temperature difference between the two sections can be controlled with the aid of the separate control.

In addition, a control of the heating rates is possible due to the fact that the first and the second sections can be heated separately. The necessity of a construction-dependent compromise between the heating rate and the delay—which compromise has to be made in the case of systems with platforms—no longer exists in the case of this system. In particular when the atomization of the analyte takes place from the secondary surface, this will also permit increased heating rates and, consequently, an improved sensitivity in the case of reduced gaseous phase interferences.

According to a preferred embodiment of the present invention, the secondary surface is a section of the inner wall of the hollow-body furnace.

This has the additional advantage that the atomization means can be produced with little effort.

In accordance with a preferred embodiment, the first and the second section can be provided with contact members by means of which electric current can be supplied to said hollow-body furnace.

For this purpose, a common contact element can be provided for both sections and two contact members which are electrically insulated from each other can be provided for said two sections.

Such an arrangement has the advantage that the atomization means can be used in known atomic absorption spectrometers without any necessity of modifying said known atomic absorption spectrometers with the exception of the current supply means and the control unit for the current supply means.

The material used for the hollow-body furnace is preferably graphite. This material guarantees that the furnace can be heated, by supplying current thereto, directly and with a very short response behaviour.

According to a special embodiment, the hollow-body furnace can have a tubular structural design. In this connection, it will be particularly suitable when the two sections have the shape of a semitube. These two semitubular sections can then be assembled so as to form a tubular body, the contact members of the two semitubes being insulated from each other on at least one side of said tubular body.

According to a special embodiment, the furnace tube of a transversely heated tubular furnace is constructed such that it is slotted in the longitudinal direction on one contact side, the slot defined in this way is provided with insulating material and the walls of the tubular furnace located on both sides of said slot are connected to separate electric contacts.

An appropriate insulator for this purpose are pyrolytic graphite, the anisotropy of this material being used in a suitable manner, or ceramic materials.

These special embodiments permit the hollow-body furnace to be produced at a low price. Furthermore, this type of embodiment of the furnace can easily be used in known atomic absorption spectrometers.

According to a further special embodiment, a dosing aperture can be provided in the first section of the furnace. By means of this aperture, the sample can be applied to the surface located opposite the secondary surface.

In this way, the analyte is distributed on the secondary surface in the best possible manner for the purpose of atomization.

According to a further embodiment of the invention, the process mentioned at the beginning can be carried out such that a hollow-body furnace is provided, which comprises a first section and a second section, which are adapted to be electrically heated independently of one another, the secondary surface being defined by a surface of said first section, that, after the application of the analyte to a surface of said second section, said surface is electrically heated so that a transfer of the analyte via the gaseous phase to the secondary surface takes place, said secondary surface being maintained at a temperature which permits the analyte to condense on said secondary surface, and that, after said transfer, the first section is electrically heated to a temperature corresponding essentially to that of the second section, whereby the analyte condensed on said secondary surface is desorbed and atomized.

An essential feature of this process is that the secondary surface of the first section and the second section are heated independently of one another. This has the effect that the time delay in the heating of the atomization surface, the control of the temperature difference between the surface to which the analyte is applied and the secondary surface onto which said analyte is to be condensed as well as the heating rate can be controlled precisely. In this way, the atomization process can be adapted to the given properties of the analytes to be detected much better than in the case of known processes. The matrix effects during atomization will be reduced in this way and, on the whole, a higher sensitivity in the case of reduced gaseous phase interferences will be obtained. It follows that, taking all this into account, smaller amounts of analyte can be detected by means of this process.

According to a special embodiment of the present process, the analyte, after having been applied to the second section, is dried by heating both sections to essentially the same temperature. When this heating is carried out synchronously and with the same temperature, a condensation of solvents or of coarse constituents on the surfaces of the atomizer can be avoided. This will especially improve the results when analytes, which are constituent parts of samples containing such components, are to be detected.

According to a further embodiment, the analyte, after having been applied to the second section, is dried by heating the first section to a temperature that is higher than the temperature of the second section so that the first section is used as a surface radiator. This permits an evaporation of samples which, when heated directly, evaporate irregularly or cause analyte losses. This process step reduces the analyte losses in the case of such samples, and, consequently, more precise measurement results will be obtained.

BRIEF DESCRIPTION OF THE DRAWINGS

In the following, the present invention will be explained in detail on the basis of preferred embodiments shown in the drawing, in which.

DETAILED DESCRIPTION OF THE PREFERRED EMBODIMENTS

Figure 1:
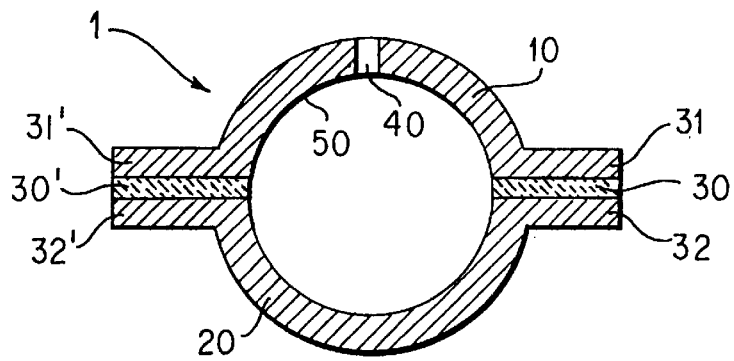
FIG. 1 shows a cross-section through an atomization means according to a first embodiment of the present invention.

FIG. 1 shows, in a cross-sectional view, an electrically heatable tubular furnace designated by reference numeral 1. This tubular furnace comprises a first section 10 and a second section 20. These two sections, which have a semitubular structural design according to FIG. 1, are separated by insulators 30 and 30', respectively.

The first semitubular section 10 is followed by contact members 31 and 31', which extend radially outwards from said section 10. The second section 20 is followed by contact members 32 and 32', respectively, in the same way. These contact members 31 and 31' as well as 32 and 32' are connected to separate current supply means (not shown) so that a current, which causes said sections 10 and 20 to be heated, can be conducted through said sections 10 and 20.

The current supply means for said two sections can be constructed such that they are programmable so that an automatic and reproducable control with regard to temperature, time and heating rates is possible.

Furthermore, various programmable gas inlets (not shown) can be provided, said gas inlets permitting different gases to be conducted into in the furnace during the steps of the heating program as well as a flow around the furnace. Such gas inlets are known e.g. from EP-A-0350722.

The first section 10 additionally comprises a dosing aperture 40. Through this dosing aperture, a sample, which will be a liquid sample in most cases, can be introduced in the furnace with the aid of a dosing capillary or an automatic dosing device (not shown).

In the embodiment shown in FIG. 1, the current is conducted through the furnace transversely to the longitudinal axis thereof; i.e. the furnace is heated in the transverse direction. This has the effect that temperature gradients over the length of the tubular atomizer are avoided. The contact members can especially have a structural design of such a nature that the first section 10 (and the second section 20, respectively ) are heated as uniformly as possible. Special embodiments for avoiding such temperature gradients and for guaranteeing uniform heating are known e.g. from EP-B-0381948.

The sections 10 and 20 are produced from a conducting material, such as graphite or tungsten. The material used as an insulator is especially pyrolytic graphite, the anisotropy of this material being used in a suitable manner. Alternatively, it is also possible to use ceramic materials as insulators.

Figure 2:
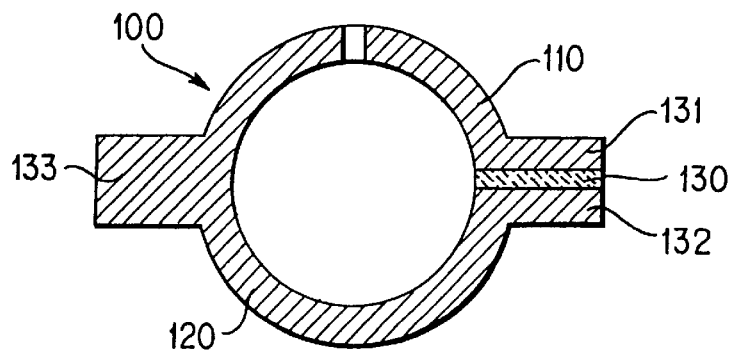
FIG. 2 shows a cross-section through an atomization means according to a second embodiment of the present invention.
Figure 4B:
FIG. 4 shows a cross-section of an atomization means according to the prior art.
Figure 4:
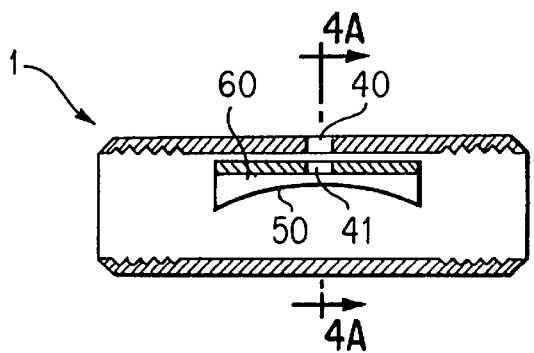
Figure 4A:
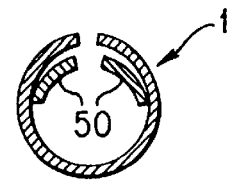

In FIG. 2, a further embodiment of the furnace 100 according to the present invention is shown. In contrast to FIG. 1, the first section 110 and the second section 120 have a common contact member 133. On the side located opposite said contact member, two contact members 131 and 132, respectively, are provided for the first section 110 and the second section 120, in a manner corresponding to the embodiment according to FIG. 1. In the embodiment according to FIG. 2, it suffices to provide a single current supply from the left side. As for the rest, the furnace corresponds to the furnace shown in FIG. 1.

In addition to the tubular furnaces which are shown in FIG. 1 and 2 and which comprise said sections 10 and 20, furnaces having a different structural design can be used as well. On the one hand, two sections having an arbitrary shape can be used, which, when assembled, define a tubular furnace body and can be heated independently of one another. On the other hand, it is also possible to use hollow bodies having some other shape.

Figure 3:
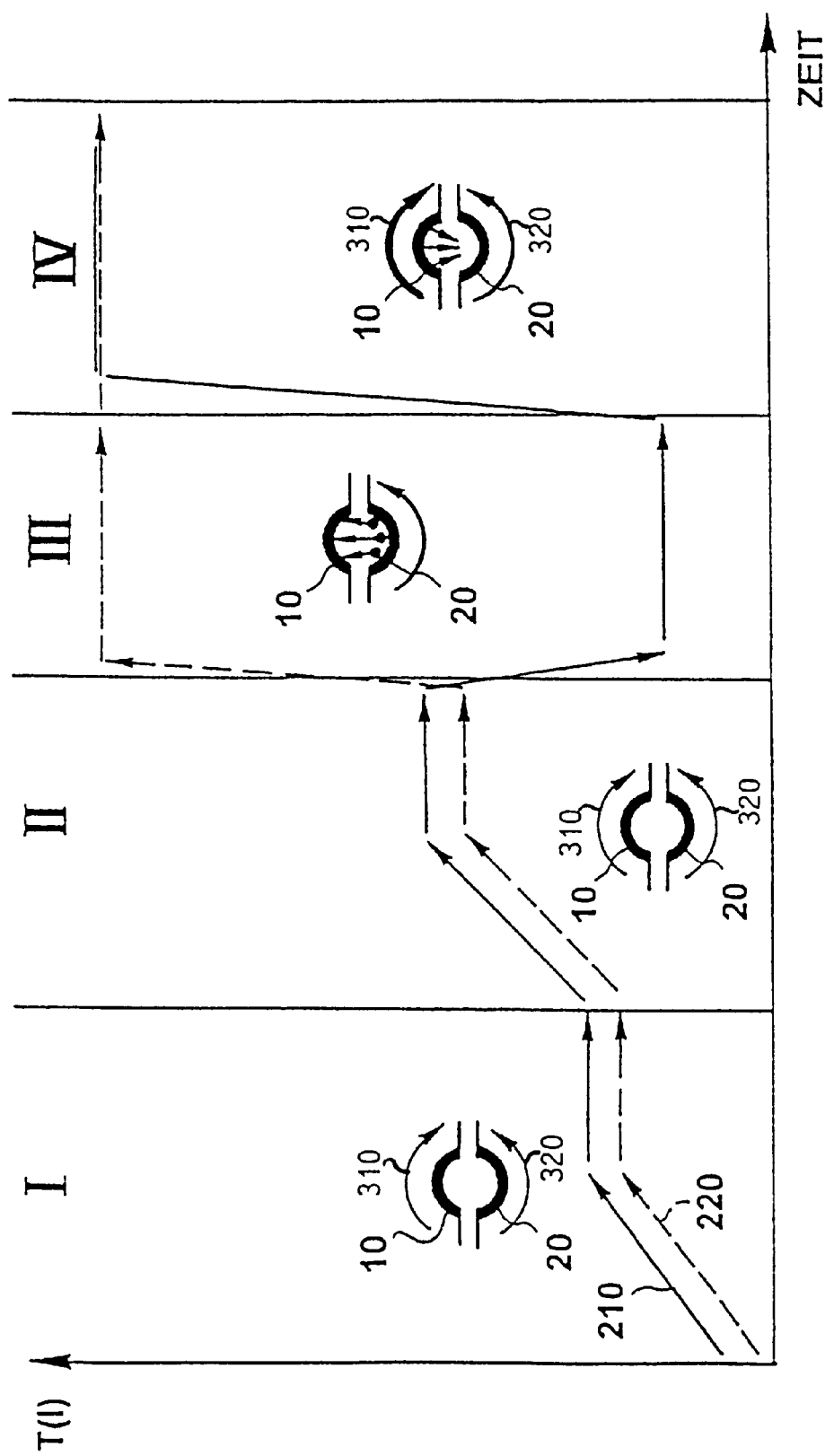
FIG. 3 shows a diagram for explaining a process according to an embodiment of the present invention.

FIG. 3 shows a diagram for explaining a process for atomizing an analyte of a sample to be examined, said process being adapted to be used in a furnace according to FIG. 1 or 2.

In this diagram, the time is shown in the horizontal direction and the temperature in the vertical direction. The time axis is subdivided into four areas I, II, III and IV. These areas represent various process steps, viz. drying, reduction to ashes, redistribution and atomization in the process according to the present invention.

For each of these process steps, the temperature (solid arrows 210) of the first section 10 and the temperature (broken arrows 220) of the second section 20 are shown. Furthermore, the furnace is schematically shown in the form of its two sections 10 and 20 for each area, the flow of current through the first section 10 and through the second section 20 being schematically outlined for each area by means of arrows 310 and 320. The thickness of the arrows 310 and 320 is representative of the flow of current through the respective area.

When the sample to be analyzed has been applied in a suitable manner to the inner side of the second section 20 through the dosing aperture 40 ( e.g. by means of an automatic dosing device), the sample is dried by programmed heating of the first and second sections 10, 20 and pyrolyzed in step I. According to FIG. 3, the first section 10 is heated to a slightly higher temperature than the second section 20 for this purpose. In this case, the first section 10 acts as a surface radiator by means of which samples can be evaporated which, when heated directly, evaporate irregularly or cause-analyte losses.

In addition to the drying process shown, it is also possible to use other heating rates, which are adapted to the respective analyte to be detected. It is, for example, possible to heat both sections synchronously and with the same temperature so as to avoid a condensation of solvents or sample components on the surfaces of the atomizer.

After the heating, the temperatures of the first section and of the second section are maintained at a constant value until the drying phase has been finished.

In step II, the sample is reduced to ashes. For this purpose, the first section 10 and the second section 20 are heated in a manner similar to the heating carried out in step I, and then they are maintained at a constant temperature until the pyrolysis has been finished.

In steps I and II, a gas can be conducted through the furnace so that substances formed during the drying step and the pyrolyzing step are discharged.

These two heating steps are followed by step III. In this step, the sample is thermally decomposed and the analyte to be detected is redistributed via the gaseous phase from said second section 20 to said first section 10. For this purpose, the second section 20 is heated very rapidly to a temperature that is suitable for atomization. The temperature of the first section 10 is either maintained at the former pretreatment temperature or, as shown in FIG. 3, lowered to a lower temperature. In view of the fact that the surface of section 10 is much colder, the analyte condenses on the secondary surface 50 of said section.

The temperature difference between the upper and the lower section can be adapted to the properties of the analyte and of the sample matrix in a controlled manner. During step III, the flow of gas through the furnace is interrupted so that, at the end of step III, the analyte is quantitatively deposited on the secondary surface 50 of the first section 10.

By means of the transfer step III, the original sample is distributed over a much larger active surface and the original sample structure, which is e.g. a crystalline sample structure in the case referred to, is destroyed. This has the consequence that the subsequent atomization of the analyte effected from the secondary surface 50 becomes independent of the original sample matrix to a very large extent.

Step III is followed by the actual atomization step IV. In this step, the first section 10 is heated to the aimed-at atomization temperature as rapidly as possible. This has the effect that the analyte deposited on the secondary surface 50 of said section 10 desorbs from said surface and is transferred to the gaseous atmosphere preheated by the second section 20.

It goes without saying that also in this step the flow of gas can be reduced or interrupted in accordance with the sensitivity required.

In step IV, an atomic absorption spectroscopy measurement can be carried out in the manner known.

When the measurement has been finished, the residual atomization products are removed from the furnace by baking out. For this purpose, gas is again conducted through the furnace.

In the table following hereinbelow, a typical example of a control in accordance with the process according to the present invention is given.

TABLE

| step | temperature (° C.) | | heating (s) | maintaining (s) | gas flow | detection |
|---|---|---|---|---|---|---|
| I: sample drying | section 20: | 110 | 5 | 10 | full | — |
| | section 10: | 250 | | | | |
| II: reduction to ashes | section 20: | 500 | 15 | 10 | full | — |
| | section 10: | 500 | | | | |
| III: redistribution | section 20: | 1800 | 0 | 0.5 | — | — |
| | section 10: | 300 | | | | |
| IV: atomization | section 20: | 1800 | 0 | 3 | — | active |
| | section 10: | 1800 | | | | |
| baking out | section 20: | 2400 | 1 | 3 | full | — |
| | section 10: | 2400 | | | | |

We claim:

1. An electrically heatable hollow-body furnace (1; 100) comprising:

a first semi-cylindrical section (10; 110) having an inner wall and an outer wall and a second semi-cylindrical section (20; 120) having an inner wall and an outer wall, said sections positioned in close relationship to form a tube, said sections designed for being electrically heated independently of one another; and, a secondary surface (50) on which an analyte of a sample to be examined is condensed prior to being converted into the atomized state for examination, said secondary surface (50) being defined by a surface of said first section (10; 110).

2. A furnace according to claim 1, wherein said secondary surface (50) is a section of the inner wall of the hollow-body furnace (1).

3. A furnace according to claim 1, wherein said first section (10; 110) and said second section (20; 120) are connected to contact members (31, 31', 32, 32'; 131, 132, 133) for supplying electric current to said hollow-body furnace (1; 100).

4. A furnace according to claim 3, wherein a common contact member (133) is provided for both sections (110, 120) and wherein two contact members (131, 132) which are electrically insulated from each other are provided for the two sections (110, 120).

5. A furnace according to claim 1, wherein the hollow-body furnace (1; 100) is comprised of graphite.

6. A furnace according to claim 1, wherein both sections are separated by at least one insulator (30; 130) so that they are heated independently of one another.

7. A furnace according to claim 6, wherein said at least one insulator (30) comprises pyrolytic graphite or ceramic materials.

8. A furnace according to claim 6, wherein the tubular furnace is designed for being heated transversely to the longitudinal direction thereof.

9. A furnace according to claim 1, wherein the first section includes a dosing aperture (40).

10. A furnace according to claim 1, wherein said first semi-cylindrical section and said second semi-cylindrical section form a single cylindrical tube.

* * * * *